US00PP22813P2

(12) United States Plant Patent van Gils et al.

(10) Patent No.: US PP22,813 P2
(45) Date of Patent: Jun. 26, 2012

(54) *THUJA* PLANT NAMED 'ANNIEK'

(50) Latin Name: *Thuja occidentalis*
Varietal Denomination: Anniek

(76) Inventors: Franciscus van Gils, Hulsel (NL); Wlodzimierz Flejszer, Skierniewice (PL)

( * ) Notice: Subject to any disclaimer, the term of this patent is extended or adjusted under 35 U.S.C. 154(b) by 24 days.

(21) Appl. No.: 12/925,949

(22) Filed: Nov. 2, 2010

(51) Int. Cl.
*A01H 7/00* (2006.01)

(52) U.S. Cl. ..... Plt./213

(58) Field of Classification Search ..... Plt./213
See application file for complete search history.

(56) References Cited

OTHER PUBLICATIONS

Pluto Upov Plant Variety Database 2011/05, Citation for *Thuja* 'Anniek', retrieved on Jan. 11, 2012. Retrieved from the Internet at <http://upov.int/pluto/en/> 2 pp.*

* cited by examiner

*Primary Examiner* — June Hwu
(74) *Attorney, Agent, or Firm* — C. A. Whealy

(57) ABSTRACT

A new and distinct cultivar of *Thuja* plant named 'Anniek' characterized by its compact plant habit and globular plant form; freely branching habit; dense and bushy form; leaves that are soft to the touch; developing leaves are yellow green in color in the spring and summer becoming bronze in color in the autumn and winter; and good winter hardiness.

4 Drawing Sheets

Botanical designation: *Thuja occidentalis.*
Cultivar denomination: 'ANNIEK'.

BACKGROUND OF THE INVENTION

The present invention relates to a new and distinct cultivar of *Thuja* plant, botanically known as *Thuja occidentalis* and hereinafter referred to by the name 'Anniek'.

The new *Thuja* plant is a naturally-occurring branch mutation of *Thuja occidentalis* 'Teddy', not patented. The new *Thuja* plant was discovered and selected by the Inventors on a single plant within a population of plants of 'Teddy' in 2005 in an outdoor nursery in Skierniewice, Poland.

Asexual reproduction of the new *Thuja* plant by hardwood cuttings in a controlled environment in Skierniewice, Poland has shown that the unique features of this new *Thuja* plant are stable and reproduced true to type in successive generations.

SUMMARY OF THE INVENTION

Plants of the new *Thuja* have not been observed under all possible environmental conditions. The phenotype may vary somewhat with variations in environment such as temperature and light intensity without, however, any variance in genotype.

The following traits have been repeatedly observed and are determined to be the unique characteristics of 'Anniek'. These characteristics in combination distinguish 'Anniek' as a new and distinct cultivar of *Thuja* plant:

1. Compact plant habit and globular plant form.
2. Freely branching habit; dense and bushy form.
3. Leaves that are soft to the touch.
4. Developing leaves are yellow green in color during the spring and summer becoming bronze in color in the autumn and winter.
5. Good winter hardiness.

Plants of the new *Thuja* can be compared to plants of the parent, 'Teddy'. Plants of the new *Thuja* differ primarily from plants of 'Teddy' in the following characteristics:

1. Plants of the new *Thuja* are more compact than plants of 'Teddy'.
2. Plants of the new *Thuja* maintain their dense plant form whereas plants of 'Teddy' tend to fall apart.
3. Plants of the new *Thuja* and 'Teddy' differ in leaf color as developing leaves of plants of 'Teddy' are green during the summer becoming brown during the winter.

Plants of the new *Thuja* can be compared to plants of *Thuja occidentalis*, 'Danica', not patented. In side-by-side comparisons, plants of the new *Thuja* differ primarily from plants of 'Danica' in leaf color as developing leaves of plants of 'Danica' are green during the summer becoming brown green during the winter.

Plants of the new *Thuja* can also be compared to plants of *Thuja occidentalis*, 'Tiny Tim', not patented. In side-by-side comparisons, plants of the new *Thuja* differ primarily from plants of 'Tiny Tim' in leaf color as developing leaves of plants of 'Tiny Tim' are green during the summer becoming brown during the winter.

BRIEF DESCRIPTION OF THE PHOTOGRAPHS

The accompanying colored photographs illustrate the overall appearance of the new *Thuja* plant showing the colors as true as it is reasonably possible to obtain in colored reproductions of this type. Colors in the photograph may differ slightly from the color values cited in the detailed botanical description which accurately describe the colors of the new *Thuja* plant.

The photograph on the first sheet comprises a side perspective view of a typical plant of 'Anniek' during the spring.

The photograph on the second sheet comprises a side perspective view of two typical plants of 'Anniek' grown during the late summer in containers.

The photograph on the third sheet comprises a side perspective view of a typical plant of 'Anniek' grown during the winter in a container.

The photograph on the fourth sheet is a close-up view of a typical plant of 'Anniek' grown during the winter.

DETAILED BOTANICAL DESCRIPTION

The aforementioned photographs and following observations, measurements and values describe plants grown in one-gallon containers in an outdoor nursery in Hulsel, The Netherlands and under conditions which closely approximate commercial *Thuja* plant production. During the production of the plants, day temperatures ranged from 8° C. to 23° and night temperatures ranged from 1° C. to 14° C. Plants were three years old when the photographs and description were taken. In the following detailed description, color references are made to The Royal Horticultural Society Colour Chart, 2007 Edition, except where general terms of ordinary dictionary significance are used.

Botanical classification: *Thuja occidentalis* 'Anniek'.

Parentage: Naturally-occurring branch mutation of *Thuja occidentalis* 'Teddy', not patented.

Propagation:

*Type*.—By hardwood cuttings.

*Time to initiate roots*.—About one month at 30° C.

*Time to produce a rooted young plant*.—About two months at 25° C.

*Root description*.—Fine to medium in thickness, fibrous; red and brown in color.

*Rooting habit*.—Fast to develop roots; freely branching; dense.

Plant description:

*Plant and growth habit*.—Perennial coniferous shrub; compact plant habit and globular plant form; low vigor to moderately vigorous growth habit.

*Plant height*.—About 12.1 cm.

*Plant diameter*.—About 13.6 cm.

*Branching habit*.—Freely branching with numerous lateral branches; dense and bushy habit.

*Lateral branch description*.—Length: About 8 cm. Diameter: About 1.5 mm. Internode length: About 1.3 cm. Strength: Strong. Texture: Smooth. Color: Developing branches: Close to 145A. Developed branches: Close to N199B and 200C tinged with close to 183B.

*Leaf description*.—Appearance/arrangement: Flattened and appressed, scale-like; opposite, simple; sessile. Length: About 3 mm. Width: About 1 mm. Shape: Lanceolate. Apex: Abruptly acute. Base: Cuneate. Margin: Entire. Venation pattern: Parallel. Fragrance: When crushed, cedar-like. Texture: Smooth, glabrous; soft to the touch. Color: Developing leaves, upper surface: During the spring and summer, close to N144C; during the autumn and winter, close to 172B to 172C. Developing leaves, lower surface: During the spring and summer, close to N144C; during the autumn and winter, close to N170B. Fully expanded leaves, upper surface: Year-round, close to 137B; venation, close to 137B. Fully expanded leaves, lower surface: Year-round, close to 143C; venation, close to 143C.

Cone description: Cone development has not been observed on plants of the new *Thuja*.

Temperature tolerance: Plants of the new *Thuja* have been observed have good winter hardiness and to be tolerant to USDA Hardiness Zone 6 and high temperatures of about 35° C.

Pathogen/pest resistance: Plants of the new *Thuja* have not been observed to be resistant to pests and pathogens common to *Thuja* plants.

It is claimed:

1. A new and distinct *Thuja* plant named 'Anniek' as illustrated and described.

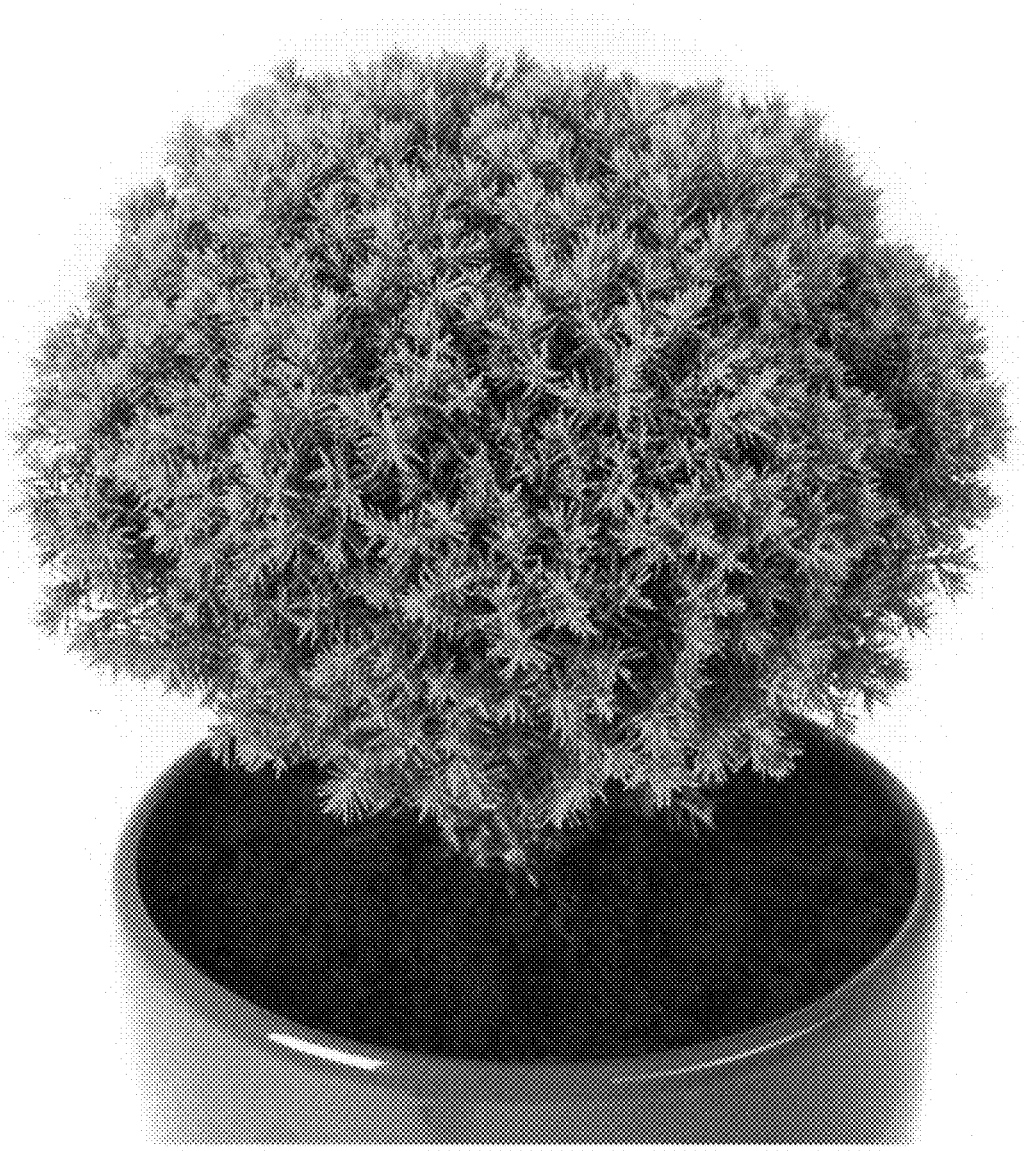

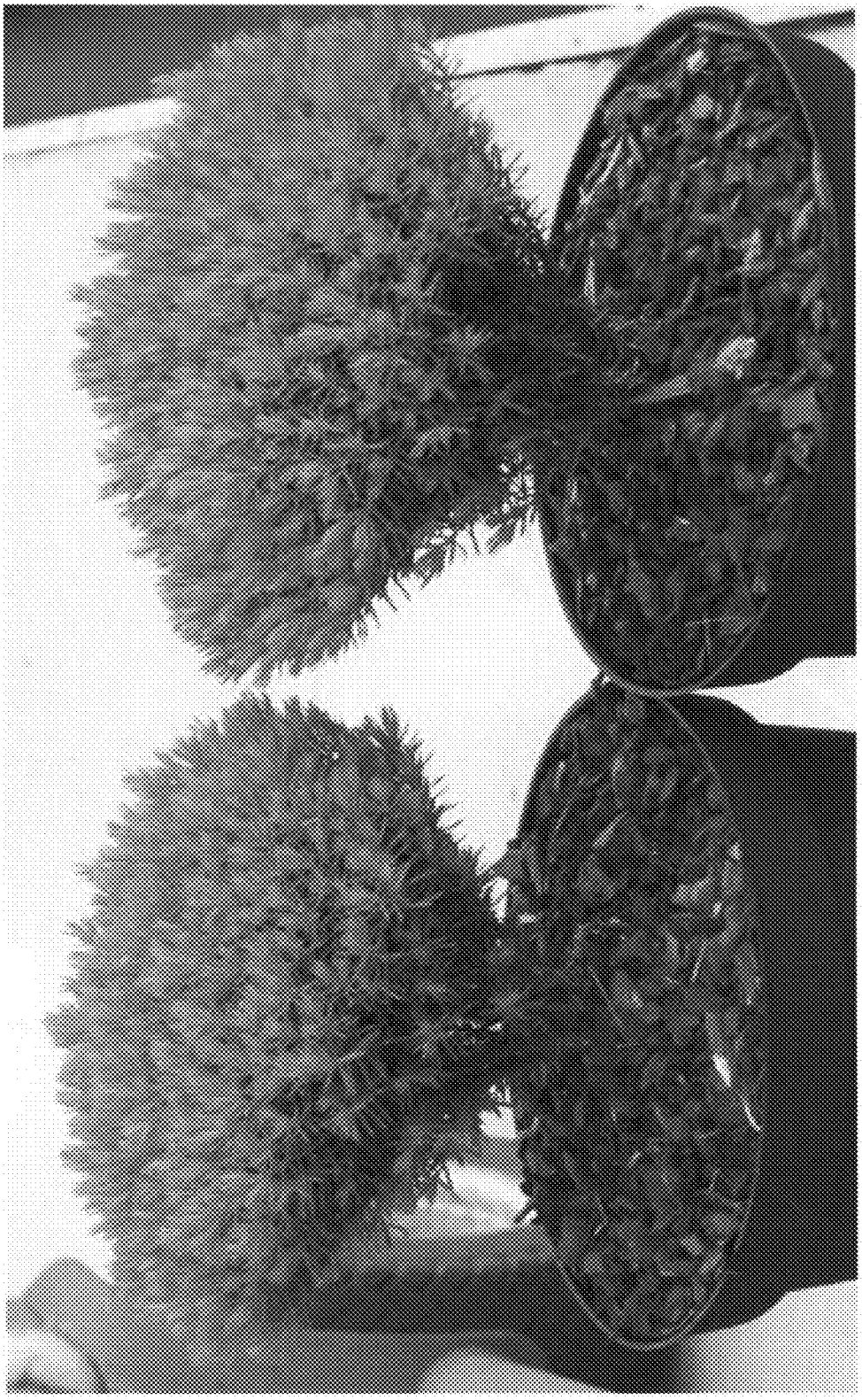

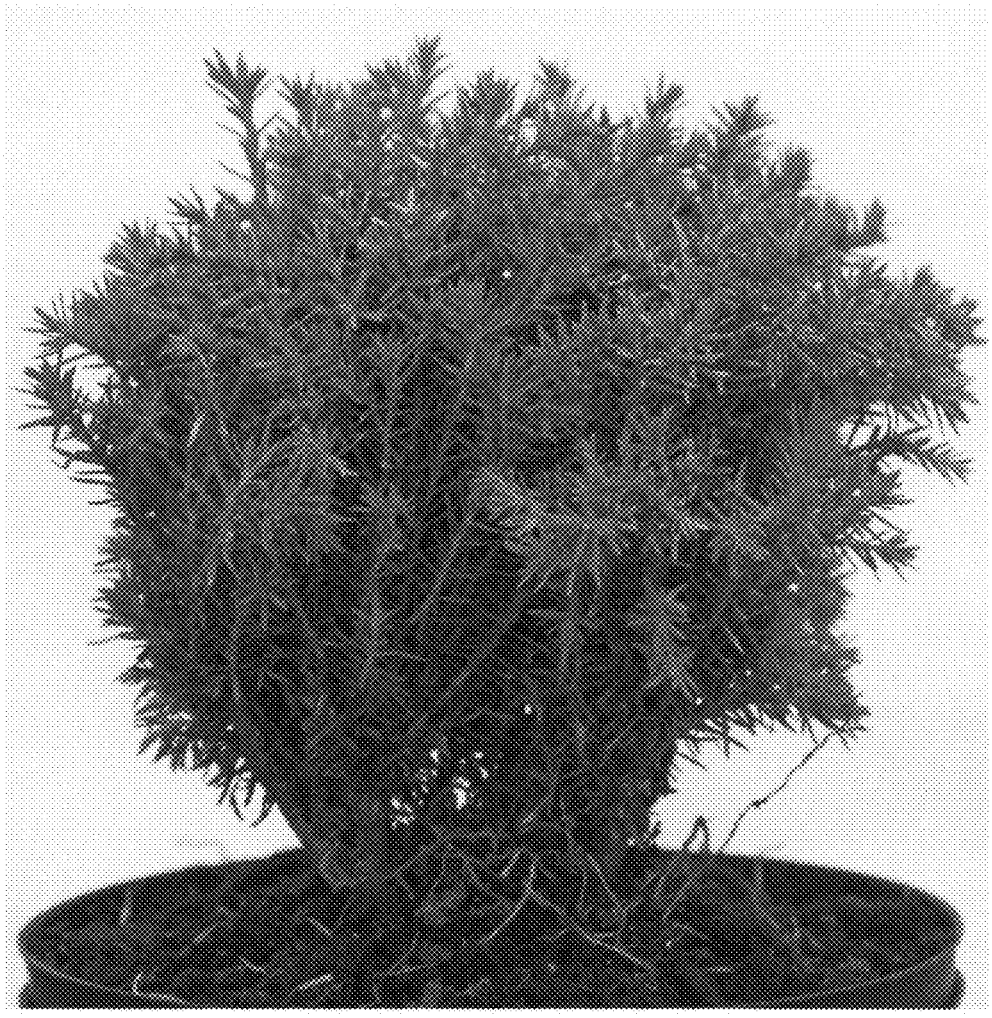

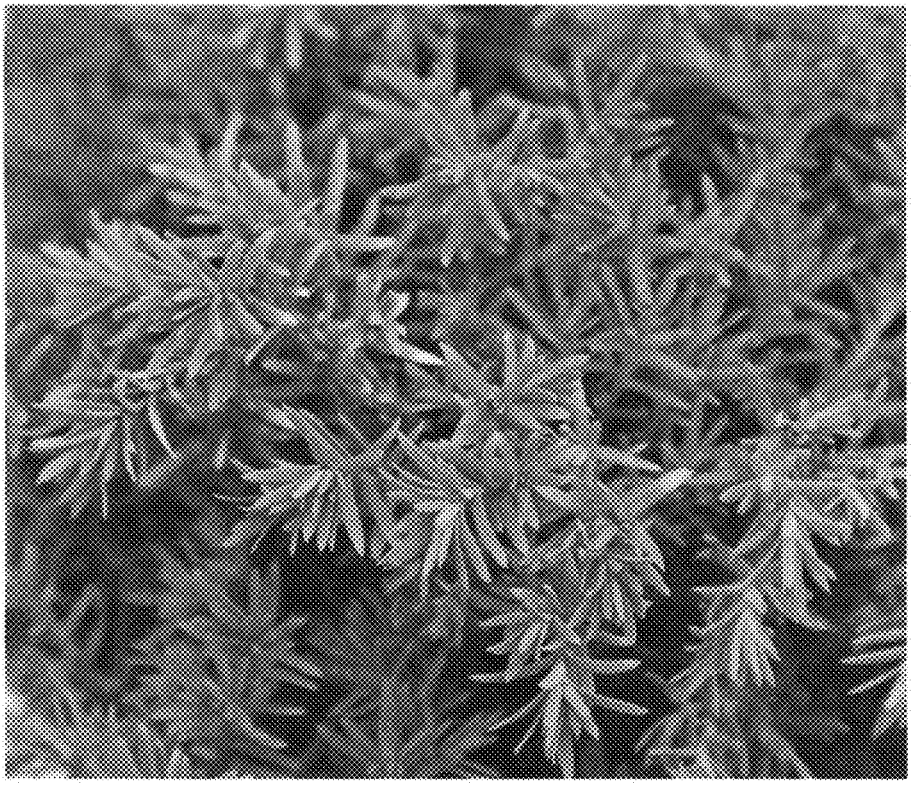

* * * * *